US006849079B1

United States Patent
Blake, III et al.

(12) United States Patent
(10) Patent No.: US 6,849,079 B1
(45) Date of Patent: Feb. 1, 2005

(54) CLIP DETENT SPRING FOR REPEATING MULTI-CLIP APPLIER

(75) Inventors: Joseph W Blake, III, New Canaan, CT (US); Kenneth J Lisk, Fairfield, CT (US)

(73) Assignee: Joseph W. Blake, III, New Canaan, CT (US)

( * ) Notice: Subject to any disclaimer, the term of this patent is extended or adjusted under 35 U.S.C. 154(b) by 0 days.

(21) Appl. No.: 10/315,970

(22) Filed: Dec. 10, 2002

(51) Int. Cl.[7] .............................................. A61B 17/12
(52) U.S. Cl. ...................... 606/143; 267/163
(58) Field of Search .................... 606/143; 267/163, 267/158, 159, 160

(56) References Cited

U.S. PATENT DOCUMENTS

| | | | | |
|---|---|---|---|---|
| 2,490,741 A | * | 12/1949 | Pashby | 72/17.3 |
| 2,927,171 A | * | 3/1960 | Rhodes | 200/456 |
| 3,263,504 A | * | 8/1966 | Parkinson et al. | 73/514.12 |
| 3,844,289 A | * | 10/1974 | Noiles | 606/143 |
| 4,152,920 A | * | 5/1979 | Green | 72/409.05 |
| 4,572,183 A | * | 2/1986 | Juska | 606/143 |
| 4,616,650 A | * | 10/1986 | Green et al. | 606/143 |
| 5,623,854 A | * | 4/1997 | Snider | 74/553 |
| 5,993,465 A | * | 11/1999 | Shipp et al. | 606/142 |
| 6,348,054 B1 | * | 2/2002 | Allen | 606/75 |
| 2002/0049472 A1 | * | 4/2002 | Coleman et al. | 606/219 |

* cited by examiner

Primary Examiner—David O. Reip
Assistant Examiner—Bradford C Pantuck
(74) Attorney, Agent, or Firm—Patrick H. Walsh

(57) ABSTRACT

A clip detent spring forming part of a mechanism for inserting clips into the jaws of a clip applying instrument performs the tasks of engaging and separating a first in line clip from a line of clips carried by the mechanism, and the task of positioning the clip for insertion into the instrument jaws.

2 Claims, 2 Drawing Sheets

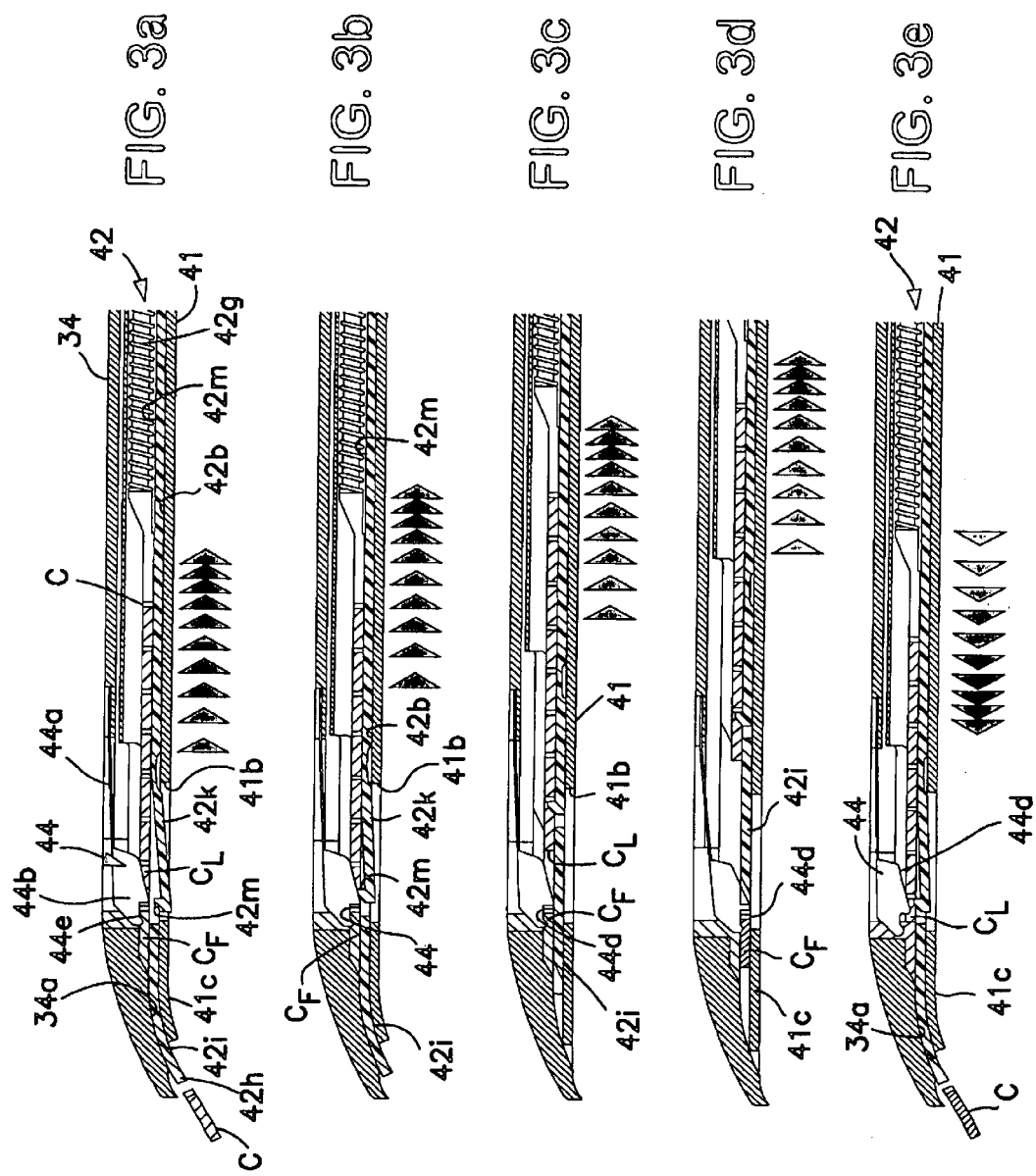

CLIP DETENT SPRING FOR REPEATING MULTI-CLIP APPLIER

BACKGROUND OF THE INVENTION

The present invention relates to surgical clip appliers embodied as an instrument having a supply of clips for rapidly deploying several clips in closing severed blood vessels and other small fluid carrying ducts in surgical procedures. There are many different designs for surgical clip applicators for a variety of surgical procedures including both open surgery and laparoscopy in which a clipping appliance fits through a trocar tube into a body cavity where the clips are applied.

A surgical clip applicator comprises an operating handle and clip applying mechanism having an operating cycle in which operating levers are squeezed together and released. In this operating cycle, a clip is applied in surgery and the clip applicator jaws are reloaded with a lead or first in line clip from a clip supply channel for clip application in the next applicator mechanism cycle. The applicator provides a moveable clip supply channel containing a line of clips that are released seriatim.

This invention provides a new and useful clip detent spring for separating the lead clip in the clip supply channel, and for moving the lead clip into a set position from which the lead clip is pushed into clip applying jaws.

SUMMARY OF THE INVENTION

A repeating multi-clip applier embodying the clip detent spring according to the present invention comprises an instrument having an operating handle housing and a removable, fully rotatable and disposable clip applying cartridge. A full squeeze and release of operating handles applies a clip to a surgical site and reloads another clip into clip applying jaws of the instrument.

The clip actuating mechanism includes a combined actuating rod and in-line clip supply channel together with clip indexing mechanisms arranged so that with a squeeze of the operating levers, the actuating rod moves rearward in the appliance to apply a clip in surgery, capture the next in-line clip, index a line of clips rearward away from the clip jaws; and that with release of the operating levers, the jaws open, the next in-line clip is loaded into the jaws, the second next in-line clip is separated from the line, and the clip indexing movement is reset for the next cycle. The clip applicator includes a novel detent spring for separating the first in line clip, and for moving the clip into position from which the clip is pushed into the operating jaws.

Specific examples are included in the following description for purposes of clarity, but various details can be changed within the scope of the present invention.

OBJECTS OF THE INVENTION

An object of the invention is to provide a clip applicator having an clip applying cartridge with a clip detent spring.

Another object of the invention is to provide a clip applicator having an clip detent spring for separating a first in line clip and for moving the separated clip into a set position from which the clip is pushed into clip applying jaws.

Other and further objects of the invention will become apparent with an understanding of the following detailed description of the invention or upon employment of the invention in practice.

BRIEF DESCRIPTION OF THE DRAWING

A preferred embodiment of the invention has been chosen for detailed description to enable those having ordinary skill in the art to which the invention appertains to readily understand how to construct and use the invention and is shown in the accompanying drawing in which:

FIGS. 3a, b, c, d and e are fragmentary section views of the sequence of (a) a clip loaded in the jaws ready to fire and clip fired, (b) next-in-line clip being detained, (c) line of clips in cartridge being indexed rearward, (d) next-in -line clip moved downward into loading position, and (e) next-in line-clip loaded into the jaws ready for firing.

DETAILED DESCRIPTION OF THE PREFERRED EMBODIMENT

Figure 1:
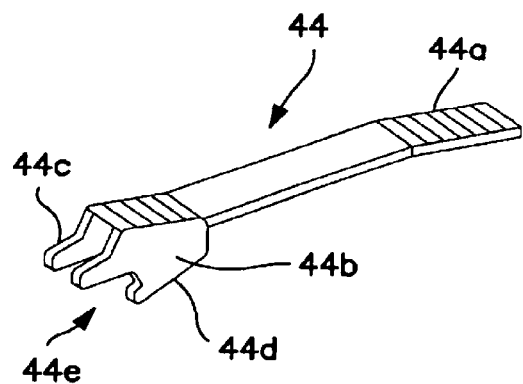
FIG. 1 is a perspective view of a clip detent spring according to the invention.
Figure 2:
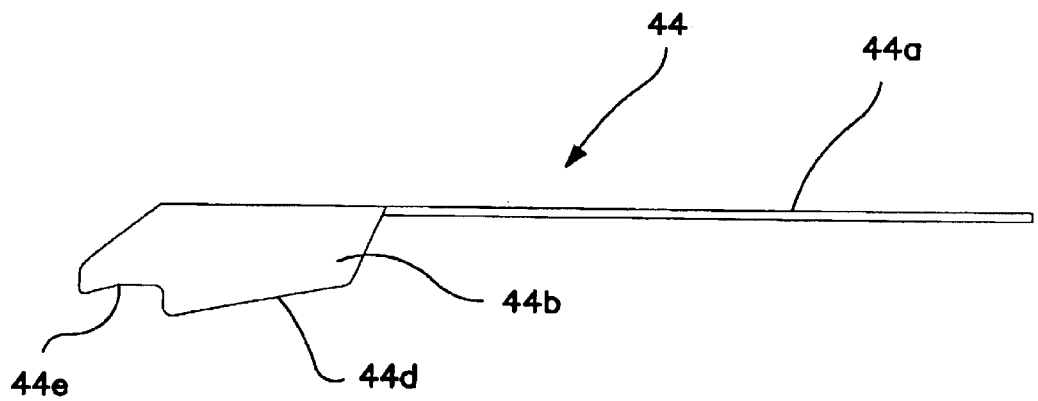
FIG. 2 is an enlarged side elevation of clip detent spring according to the invention.

Referring to the drawing, the clip applying mechanism shown in FIGS. 3a–e includes a stationary housing upper shell 34 and a stationary clip plate 41. The upper housing shell supports the clip detent spring 44 and has a guide ramp surface 34a for positioning clips for movement into clip applying jaws (not shown).

A movable clip supply magazine 42 is positioned between shell 34 and clip plate 41. The movable clip supply magazine receives a line of clips C urged forward within the magazine by a clip follower 42b and coil spring 42g. The magazine has an integral base plate 42b with integral clip stop spring 42k and a forward pusher plate 42i.

An operating handle (not shown) provides linear reciprocating motion to the clip supply mechanism such that the clip supply magazine slides back and forth (see arrows in FIGS. 3a–e) with respect to the stationary housing and clip plate.

A preferred embodiment of the clip detent spring comprises a leaf spring tang 44a with spaced depending panels 44b–c of identical edge contour including inclined rear edges 44d terminating in forwardly directed notches 44e for engaging the shoulders of a lead clip to separate the lead clip from the line as the line of clips and the clip magazine are pulled rearward by clip stop spring 42k with a pull of the operating handle. On release of the handle and consequent forward movement of the clip magazine (FIGS. 3d–e), the cartridge pusher plate 42i engages the rear surface of the detained lead clip and pushes it into the crimping jaws.

The action of clip moving components is shown in FIGS. 3a–e starting with FIG. 3a which shows components in forward position and a clip $C_J$ in the instrument jaws.

Referring to FIG. 3a, a first in line of clips $C_F$ is at rest under the detent spring notches 44e for the purpose of separating clip $C_F$. The detent spring 44 is stationary in that it is affixed to the under side of the housing cover 34 in position to capture and hold the lead clip $C_F$ at the end of the forward excursion of the clip supply magazine. The detent spring takes and separates the lead clip $C_F$ from the clip line in preparation for movement of the lead clip into the applicator jaws on a subsequent applicator cycle. The detent spring separates clip $C_F$ by reaction as the inclined rear edges 44d ride up (FIG. 3e) on forwardly moving clip $C_F$ and snap down (FIG. 3a) as the clip passes the shoulders. Such clip capture occurs as the clip magazine reciprocates during operation of the applicator.

From the position of FIG. 3a, a rearward pull of the operating handle begins immediate rearward sliding movement of clip supply magazine 42 with respect to stationary upper shell 34 and stationary clip plate 41. The clip detent spring 44 holds and separates clip $C_F$ from the line of clips. The line of clips moves rearward with the clip cartridge as clip stop spring 42k is cammed upward (FIG. 3b) by cam slot 41b in clip plate 41. As movement continues (FIG. 3c), the cartridge pusher plate 42i also moves rearward sliding underneath clip $C_F$ and coming to rest behind the clip (FIG. 3d) at the end of the rearward stroke of the operating handles. As pusher plate 42i slides behind clip $C_F$, the clip detent spring 44 (having a normal downward spring force) pushes clip $C_F$ downward into contact with clip ramp 41c. When the operating handles are released, beginning from the position of FIG. 3d and continuing to FIG. 3e, the clip cartridge pusher plate 42i engages clip $C_F$, pushes it forward between upper shell ramp surface 34a and clip plate ramp 41c and on into the instrument jaws. As this forward motion occurs, the clip detent spring 44 rides up on clip $C_L$ with notches 44d coming to rest behind the clip shoulder as illustrated in FIG. 3a.

Various changes may be made to the structure embodying the principles of the invention. The foregoing embodiments are set forth in an illustrative and not in a limiting sense. The scope of the invention is defined by the claims appended hereto.

We claim:

1. In a mechanism for inserting clips into the jaws of a clip applying instrument, each clip having a shoulder, the mechanism having a stationary upper housing and a stationary clip plate, a clip supply magazine positioned between the upper housing and the clip plate, the magazine adapted to receive a line of clips and to move in rearward and forward motions, the magazine further having an integral base plate with clip stopping spring and a forward pusher plate, the improvement which comprises:

a clip detent spring in the form of a leaf spring tang having a normally downward spring force affixed to the upper housing, the clip detent spring having spaced depending panels with substantially identical peripheral edges terminating in notches forwardly directed along the line of clips for engaging the shoulder of a clip to separate a clip from the line of clips as the clip magazine and line of clips undergo rearward motion and for moving the clip downward so that on forward motion of the clip magazine the pusher plate moves the lead clip into the instrument jaws.

2. In a mechanism for inserting clips into the jaws of a clip applying instrument, each clip having a shoulder, the mechanism having a stationary upper housing and a stationary clip plate, a clip supply magazine positioned between the upper housing and the clip plate, the magazine adapted to receive a line of clips and to move in rearward and forward motions, the magazine further having an integral base plate with clip stopping spring and a forward pusher plate, the improvement which comprises:

a clip detent spring in the form of a leaf spring tang having a normally downward spring force affixed at one end to the upper housing and extending along the line of clips, the clip detent spring having spaced depending: panels extending from the spring tang downwardly toward the line of clips, the panels having substantially identical peripheral edges extending in the direction of the line of clips and terminating in notches forwardly directed along the line of clips for engaging the shoulder of a clip to separate a clip from the line of clips as the clip magazine and line of clips undergo rearward motion and for moving the clip downward so that on forward motion of the clip magazine the pusher plate moves the lead clip into the instrument jaws.

* * * * *